(12) United States Patent
Humble et al.

(10) Patent No.: US 7,112,686 B2
(45) Date of Patent: Sep. 26, 2006

(54) PROCESS FOR THE PREPARATION OF RACEMIC CITALOPRAM AND/OR S-OR R-CITALOPRAM BY SEPARATION OF A MIXTURE OF R-AND S-CITALOPRAM

(75) Inventors: Rikke E. Humble, Copenhagen (DK); Troels V. Christensen, Holbaek (DK); Michael H. Rock, Hvidovre (DK); Ole Nielsen, Valby (DK); Hans Petersen, Vanlose (DK); Robert Dancer, Hvidovre (DK)

(73) Assignee: H. Lundbeck A/S, Valby-Copenhagen (DK)

( * ) Notice: Subject to any disclaimer, the term of this patent is extended or adjusted under 35 U.S.C. 154(b) by 0 days.

(21) Appl. No.: 10/482,000

(22) PCT Filed: Jun. 25, 2002

(86) PCT No.: PCT/DK02/00426

§ 371 (c)(1),
(2), (4) Date: Feb. 9, 2004

(87) PCT Pub. No.: WO03/000672

PCT Pub. Date: Jan. 3, 2003

(65) Prior Publication Data

US 2004/0259940 A1    Dec. 23, 2004

(30) Foreign Application Priority Data

Jun. 25, 2001  (DK)  .............. 2001 00991

(51) Int. Cl.
*C07D 307/78*  (2006.01)
*C07D 307/87*  (2006.01)
*C07D 307/93*  (2006.01)

(52) U.S. Cl. ............. 549/476; 549/469; 549/471

(58) Field of Classification Search ........... 549/467, 549/469, 471
See application file for complete search history.

(56) References Cited

U.S. PATENT DOCUMENTS 4,943,590 A * 7/1990 Boegesoe et al. ........... 514/469
6,566,540 B1 * 5/2003 Rock et al. ................. 549/467

FOREIGN PATENT DOCUMENTS

EP    0 347 066 B1    3/1995

OTHER PUBLICATIONS

Hackh's Chemical Dictionary, Julius Grant, p. 567.*
Rochat et al., Determination of the Enantiomers of Citalopram, Its Demethylated and Propionoc Acid Metabolites in HUman Plasma by Chiral HPLC, Chirality, pp. 389-395.*

* cited by examiner

Primary Examiner—D. Margaret Seaman
Assistant Examiner—Niloofar Rahmani
(74) Attorney, Agent, or Firm—Darby & Darby

(57) ABSTRACT

The invention relates to a process for the preparation of racemic citalopram free base or an acid addition salt thereof and/or R- or S-citalopram as the free base or an acid addition salt thereof by separation of a mixture of R- and S-citalopram with more than 50% of one of the enantiomers into a fraction consisting of racemic citalopram and/or a fraction of S-citalopram or R-citalopram characterized in that i) citalopram is precipitated from a solvent as the free base or as an acid addition salt thereof; ii) the precipitate formed is separated from the mother liquor; iia) if the precipitate is crystalline it is optionally recrystallised one or more times to form racemic citalopram, and then optionally converted into an acid addition salt thereof; iib) if the precipitate is not crystalline, steps i) and ii) are optionally repeated until a crystalline precipitate is obtained and the crystalline precipitate is recrystallised one or more times to form racemic citalopram, and then optionally converted into an acid addition salt thereof; iii) the mother liquor is optionally subjected to further purification and S-citalopram or R-citalopram is isolated from the mother liquor and optionally converted into an addition salt thereof.

27 Claims, No Drawings

PROCESS FOR THE PREPARATION OF RACEMIC CITALOPRAM AND/OR S-OR R-CITALOPRAM BY SEPARATION OF A MIXTURE OF R-AND S-CITALOPRAM

This application is a § 371 national stage of International Application No. PCT/DK02/00426, filed Jun. 25, 2002, which was published in English as International Publication No. WO 03/000672, and claims the benefit of priority of Danish Patent Application No. PA 2001 00991, filed Jun. 25, 2001.

The invention relates to a process for the preparation of racemic citalopram and/or S- or R-citalopram by separation of a mixture of R- and S-citalopram with more than 50% of one of the enantiomers into; a fraction of racemic citalopram and/or a fraction of S-citalopram or R-citalopram containing low amounts of the other enantiomer. The invention also relates to a process for the preparation of racemic as well as enantiomerically pure citalopram from the compound R-4-[4-(dimethylamino)-1-(4'-fluorophenyl)-1-hydroxybutyl]-3-(hydroxymethyl)-benzonitrile.

BACKGROUND OF THE INVENTION

S-citalopram (escitalopram) is the active component of the product citalopram, which is a racemic mixture of the R- and S-enantiomers. The compound is a valuable antidepressant of the selective serotonin reuptake inhibitor (SSRI) type.

Both racemic citalopram and S-citalopram are marketed as antidepressant agents.

It has now surprisingly been found that a mixture of R- and S-citalopram containing more than than 50% of one or the enantiomers, i.e a non-racemic mixture, may be separated into a fraction of racemic citalopram and a fraction of S- or R-citalopram by precipitation of citalopram as the free base or as an acid addition salt thereof. The surplus of S-citalopram or R-citalopram may be isolated from the mother liquor of the precipitation.

This is an important and very useful process, in particular because it allows the preparation of racemic citalopram and S-citalopram from mixtures of R- and S-citalopram obtained from manufacturing processes which result in mixtures which do not meet the specifications of the marketing approval of neither racemic citalopram nor S-citalopram (in escitalopram, the amount of R-citalopram compared to S-citalopram should be less than 3%, preferably less).

S-citalopram may be prepared by separation of the R- and S-4-[4-(dimethylamino)-1-(4'-fluorophenyl)-1-hydroxybutyl]-3-(hydroxymethyl)-benzonitrile (the R- and S-diol) followed by ring closure of the S-diol with retention of configuration, as described in EP-B1-347 066.

Other processes for the preparation of S-citalopram including chromatographic separation of enantiomers are also available. It is for example possible to separate the corresponding bromo-derivative, 1-(4-Bromo-2-hydroxymethylphenyl)-4-dimethylamino-1-(4-fluorophenyl)butan-1-ol from the corresponding R-diol, followed by ring closure with retention of configuration and cyanation to form S-citalopram. Cyanation processes for citalopram are well known and have been described in U.S. Pat. No. 4,136,193, WO 00/11926 and WO 00/13648.

Depending on the specific process used and the conditions used, the enantiomeric purity of the S-citalopram product obtained may have to be improved.

Other processes for stereo-selective synthesis of S-citalopram may also result in mixtures of R-and S-citalopram which do not fulfil the specifications of the marketing approval of S-citalopram.

Thus, according to one aspect of the invention, the invention provides an easy way to improve the enantiomeric purity of S-citalopram obtained by such processes.

During the production of S-citalopram by chromatographic separation of R- and S-4-[4-(dimethylamino)-1-(4'-fluorophenyl)-1-hydroxybutyl]-3-(hydroxymethyl)-benzonitrile followed by ring closure of S-4-[4-(dimethylamino)-1-(4'-fluorophenyl)-1-hydroxybutyl]-3-(hydroxymethyl)-benzonitrile, the R-enantiomer of formula (I)

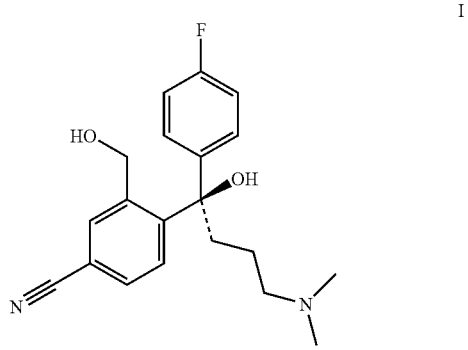

is formed as a by-product.

It has now been found that ring closure of a compound of formula I in an acidic environment provides a reaction mixture containing a surplus of S-citalopram compared to R-citalopram. In other words, ring closure in an acidic environment proceed with partial inversion of configuration.

Accordingly, the by-product of formula (I) may be used for the preparation of S-citalopram and racemic citalopram and the method for the production of S-citalopram has thereby become more rational and more economical in the utilisation of reagents and resources.

SUMMARY OF THE INVENTION

Thus, the present invention relates to a process for the preparation of racemic citalopram free base or an acid addition salt thereof and/or R- or S-citalopram as the free base or an acid addition salt thereof by separation of a mixture of R- and S-citalopram with more than 50% of one of the enantiomers into a fraction consisting of racemic citalopram and/or a fraction of S-citalopram or R-citalopram characterized in that i) citalopram is precipitated from a solvent as the free base or as an acid addition salt thereof;
ii) the precipitate formed is separated from the mother liquor;
  iia) if the precipitate is crystalline it is optionally recrystallised one or more times to form racemic citalopram, and then optionally converted into an acid addition salt thereof;
  iib) if the precipitate is not crystalline, steps i) and ii) are optionally repeated until a crystalline precipitate is obtained and the crystalline precipitate is optionally recrystallised one or more times to form racemic citalopram, and then optionally converted into an acid addition salt thereof;

iii) the mother liquor is optionally subjected to further purification and S-citalopram or R-citalopram is isolated from the mother liquor and optionally converted into an acid addition salt thereof.

According to one specific embodiment, the invention relates to a method for the preparation of racemic citalopram free base or an acid addition salt thereof using the process described above.

According to another specific embodiment, the invention relates to a method for the preparation of R- or S-citalopram free base or an acid addition salt thereof using the process described above.

The acid used for precipitation of a citalopram salt in step i) is an acid which may precipitate a mixture of R- and S-enantiomer and leave the mother liquor enriched with either the S- or R-enantiomer of citalopram. One such acid is hydrobromic acid.

According to a preferred embodiment of the invention, the free base of citalopram or the hydrobromide salt of citalopram is precipitated, preferably in crystalline form in steps i) and ii).

According to another embodiment of the invention, the mixture of R-and S-citalopram used in step i) contains more than 50% of S-citalopram, or more preferred more than 90% of S-citalopram.

In step iii) S-citalopram (or R-citalopram) may be is isolated from the mother liquor by the evaporation of the mother liquor and thereafter optionally the conversion of S-citalopram (or R-citalopram) into an acid addition salt thereof, preferably the oxalate salt.

Alternatively, if the mother liquor obtained from the precipitation is acidic, S-citalopram (or R-citalopram) may be isolated from the mother liquor by basifying the mother liquor, followed by phase separation, or extraction with a solvent and evaporation of the solvent, and thereafter optionally conversion of S-citalopram (or R-citalopram) into an acid addition salt thereof, preferably the oxalate salt.

The mother liquor, extracts thereof, or the phase containing R- or S-citalopram may be subjected to conventional purification processes (such as treatment with active carbon, chromatography, etc.) and/or it may be subjected to further precipitations as in step i)–ii) above before R- or S-citalopram is isolated.

The mixture of R- and S-citalopram with more than 50% of the S-enantiomer may be prepared from a mixture of R- and S-4-[4-(dimethylamino)-1-(4'-fluorophenyl)-1-hydroxybutyl]-3-(hydroxymethyl)-benzonitrile with more than 50% of the S-enantiomer by formation of a labile ester group and thereafter ring closure in a basic environment.

In another embodiment of the invention, the mixture of R- and S-citalopram with more than 50% of the R-enantiomer is prepared from a mixture of R- and S-4-[4-(dimethylamino)-1-(4'-fluorophenyl)-1-hydroxybutyl]-3-(hydroxymethyl)-benzonitrile with more than 50% of the R-enantiomer by formation of a labile ester group and thereafter ring closure in a basic environment.

In a further embodiment of the invention, the mixture of R- and S-citalopram with more than 50% of the S-enantiomer is prepared from a mixture of R- and S-4-[4-(dimethylamino)-1-(4'-fluorophenyl)-1-hydroxybutyl]-3-(hydroxymethyl)-benzonitrile with more than 50% of the R-enantiomer by ring closure in presence of an acid.

In still a further embodiment of the invention, the mixture of R- and S-citalopram with more than 50% of the R-enantiomer is prepared from a mixture of R- and S-4-[4-(dimethylamino)-1-(4'-fluorophenyl)-1-hydroxybutyl]-3-(hydroxymethyl)-benzonitrile with more than 50% of the S-enantiomer by ring closure in presence of an acid.

Preferably, the enantiomeric purity of the starting material R-4-[4 (dimethylamino)-1-(4'fluorophenyl)-1-hydroxybutyl]-3-(hydroxymethyl)-benzonitrile is more than 90%.

The acid used in the acidic ring closure reaction may suitably be a mineral acid such as $H_2SO_4$ or $H_3PO_4$, a carboxylic acid, a sulfonic acid or a sulfonic acid derivative.

Whenever used in this document, racemic mixture or racemic citalopram means a 1:1 mixture of R- and S-citalopram. Non-racemic mixtures or non-racemic citalopram means mixtures which do not contain R- and S-citalopram as a 1:1 mixture.

Citalopram means a mixture of R- and S-citalopram. Citalopram enantiomer or isomer means either S- or R-citalopram.

As used in this description, precipitation means forming a precipitate in the form of crystals, an amorphous solid or an oil from a solvent. In the present description, a precipitate means an oil, an amorphous solid or crystals.

As used herein, mother liquor means the solvent remaining after removal or separation from the precipitate.

DETAILED DESCRIPTION OF THE INVENTION

As mentioned above processes for the preparation of the citalopram molecule may result in a mixture of R-and S-citalopram which is not acceptable for pharmaceutical use. According to the invention, a surprisingly efficient process for the separation of such mixtures into a racemic fraction and a fraction of S-citalopram or R-citalopram has been found. This new process involves precipitation of citalopram free base or an acid addition salt thereof as an oil, an amorphous solid or in crystalline form from a solvent, and isolation of S-citalopram (or R-citalopram) from the mother liquor of the precipitation process.

The precipitation of the citalopram free base may be carried out by obtaining or dissolving the non-racemic mixture of R- and S-citalopram in a suitable solvent, optionally by applying heating, and then allowing the solution to cool. The precipitate is then separated from the mother liquor, preferably by filtration or decanting. If the precipitate is crystalline, the crystals are optionally recrystallised and the free base of racemic citalopram may then be converted to a salt thereof, preferably the hydrobromide salt.

If the precipitate formed is an oil or an amorphous solid, the precipitation process may be repeated until a crystalline product is obtained. The crystals obtained are optionally recrystallised and the free base of racemic citalopram may then be converted to a salt thereof, preferably the hydrobromide salt.

Depending on the ratio of R- and S-citalopram in the starting material, it may be necessary to precipitate (in particular crystallise) citalopram free base more than once in order to obtain racemic citalopram. The mother liquors from each precipitation may be pooled together and the citalopram enantiomer contained herein may be isolated as described below.

Suitable solvents for the precipitation of the citalopram free base are alkanes, such as heptane or hexane, alcohols, such as isopropanol, aromatic compounds such as toluene, benzene and xylene, or mixtures of alcohol and water and mixture of alkanes and alcohols. Thus, both aprotic and protic solvent may be useful.

If necessary crystallisation may be initiated by seeding with racemic crystalline citalopram base.

The precipitation of an acid addition salt of citalopram may be carried out by obtaining or dissolving the non-racemic mixture of R- and S-citalopram in a suitable solvent, if necessary by applying heating, and then adding an acid, either in a solution or as a gas. If crystals are formed, the crystals are separated from the mother liquor, preferably by filtration. The crystals are optionally re-crystallised by dissolving the crystals in a solvent, preferably by heating, and allowing the solution to cool.

If the precipitate formed is not crystalline, but amorphous or an oil, the precipitation process may be repeated until a crystalline product is obtained. The crystals obtained are optionally recrystallised as described above and the racemic citalopram salt may optionally be converted into another salt thereof.

Depending on the ratio of R- and S-citalopram in the starting material, it may be necessary to precipitate (in particular crystallise) the citalopram salt more than once in order to obtain a racemic mixture. The mother liquors from each precipitation or crystallisation may be pooled together and the citalopram enantiomer contained herein may be isolated as described below.

The acid used for precipitation of a citalopram salt is an acid which may precipitate a mixture of R- and S-enantiomer and leave the mother liquor enriched with either the S- or R-enantiomer of citalopram. One such acid is hydrobromic acid.

Suitable solvents for the precipitation and recrystallisation of citalopram salts are protic solvents such as water, alcohols such as methanol and ethanol, ketones such as acetone, and mixtures thereof or aprotic solvent such as acetonitrile or diglyme.

If necessary crystallisation may be initiated by seeding with the racemic crystalline citalopram salt.

Crystallisation of the free base or the hydrobromide salt of citalopram is preferred.

S-citalopram (or R-citalopram) may be isolated from the mother liquor using conventional procedures such as by evaporation of the solvent from the mother liquor, or in case the mother liquor is acidic by basifying followed by separation of phases (if it is an oil) or by extracting S-citalopram (or R-citalopram) followed by evaporation of the solvent. S-citalopram (or R-citalopram) may then be converted to a salt thereof, preferably the oxalate salt and optionally re-crystallised.

The mother liquor or extracts thereof may be subjected to conventional purification processes before evaporation of the solvent, or it may be subjected to one or more precipitations of citalopram free base or citalopram salt according to the invention, in order to improve the enantiomeric purity of the citalopram enantiomer product.

Likewise, an oily phase separated from the mother liquor may be subjected to conventional purification processes, or it may be subjected to one or more precipitations of citalopram free base or citalopram salt according to the invention, in order to improve the enantiomeric purity of the citalopram enantiomer product.

In another aspect of the invention it has been found that ring closure of the by-product of formula I in an acidic environment provides a reaction mixture containing a surplus of the S-enantiomer.

The process is illustrated in the reaction scheme below:

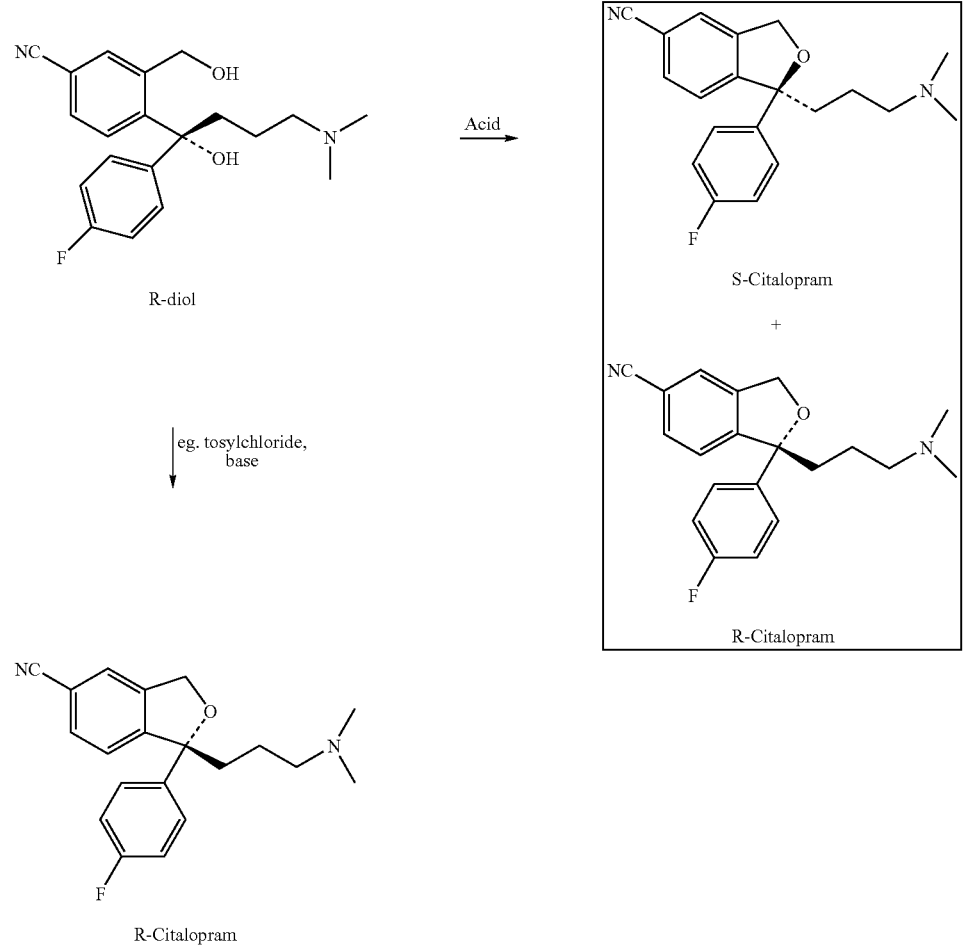

When the reaction is performed in the presence of an acid, a mixture of R-citalopram and S-citalopram is obtained from R-diol. The stereochemistry in this reaction is partly inverted, resulting in surplus of S-citalopram. The surplus amount of S-citalopram relative to R-citalopram is dependent upon the S/R ratio of the starting material as demonstrated below. The ratio of inversion versus retention is around 70:30 to 75:25 dependent on the reaction conditions of the experiment.

A surplus of S-citalopram will exist if an 4-[4-(dimethylamino)-1-(4'-fluorophenyl)-1-hydroxybutyl]-3-(hydroxymethyl)-benzonitrile with more than 50% of the R-enantiomer is used as the starting material. This resulting mixture can be further purified to give an S/R ratio of more than 95/5 by precipitation of the citalopram base from a solvent or by precipitation as an acid addition salt of citalopram from a solvent. A pure S-citalopram (S/R ratio more than 97/3) may be isolated from the mother liquor, and precipitated as an acid addition salt with an acid, such as oxalic acid.

As mentioned above, the stereochemistry is partly inverted when the ring closure of R- and S-4-[4-(dimethylamino)-1-(4'-fluorophenyl)-1-hydroxybutyl]-3-(hydroxymethyl)-benzonitrile is carried out in an acidic environment. Any suitable acid may be useful for this ring closure reaction. Good results were obtained with mineral acids such as sulphuric acid, HCl and phosphoric acid, and organic acids such as p-toluenesulphonic acid. In a preferred embodiment of the invention, sulphuric acid is used. Preferably, surplus amount of acid relative to starting material should be used.

The reaction can be performed in organic solvents suitable for dissolving the starting materials. Preferred solvents are solvents suitable for large-scale chemical production. Good results were obtained using toluene or acetonitrile.

When ring closure of the starting material of formula (I) is performed via a labile ester intermediate, ie. in the presence of tosyl-chloride, in a basic environment, as described in EP-B1-347 066, the ring closing reaction proceeds with retention of the stereochemistry. The R-form of citalopram in an enantiomeric purity substantially equal to the starting material is then obtained.

This, thus-obtained R-form of citalopram can be optionally mixed with a mixture of R and S-citalopram with an S-citalopram surplus to obtain racemic citalopram. Racemic citalopram may be obtained by one or more precipitations of citalopram free base or a salt thereof, followed by recrystallisation as described above.

EXAMPLES

In the following examples optical purity is measured by Chiral HPLC.

Example 1

Preparation of Citalopram from R-4-[4-(dimethylamino)-1-(4'-fluorophenyl)-1-hydroxybutyl]-3-(hydroxymethyl)-benzonitrile (R/S ratio: 95.7/4.3) by Reaction with different acids in acetonitrile General Method:

R-4-[4-(dimethylamino)-1-(4'-fluorophenyl)-1-hydroxybutyl]-3-(hydroxymethyl)-benzonitrile (67.5 g, R/S ratio: 95.7/4.3) dissolved in acetonitrile (37 g) was stirred at room temperature, and a mixture of acid and ice (or water) was added (the quantity of acid and ice are listed in Table 1). The mixture was stirred at 78–85° C. (the reaction time have been listed in Table 1). The reaction mixture was cooled and water and toluene (315 mL) were added. Aqueous ammonia (25% by weight) was added to give a pH 9.5–10.5 and the mixture was heated to 50–55° C. (5–10 minutes). The phases were separated and to the water phase was added toluene (50 mL), and the phases was stirred at 50–55° C. (5–10 minutes). The phases were separated and the combined toluene phases were washed three times with water (3×65 mL). The toluene was removed at reduced pressure at a maximum of 60° C. to give the product as an oil.

Citalopram was prepared by the general method above. The type of acid and the quantities of acid and ice (water) in the acid mixture are listed in Table 1. The percentage of the citalopram that is S-citalopram, analysed by chiral HPLC, is listed in Table 1 as well.

TABLE 1

Citalopram by reaction with different acids in acetonitrile.

| Example | Acid type | Mass of acid | Mass of ice or water in mixture | Reaction time | Percent S-citalopram | Yield |
|---|---|---|---|---|---|---|
| 1 | Sulphuric acid | 25 g | 10 g ice | 3 hours | 73.4 | 65.6 g (~100%) |
| 2 | Sulphuric acid | 87 g | 35 g ice | 3 hours | 72.0 | 57.0 g (89%) |
| 3 | Hydrochloric acid | 22 g | 11 g ice | 24 hours | >65 | 64.6 g (~100%) |
| 4 | p-Toluenesulfonic acid | 43 g | 40 g water | 48 hours | 73.0 | 61.6 g (95%) |

Example 2

Preparation of Citalopram from R-4-[4-(dimethylamino)-1-(4'-fluorophenyl)-1-hydroxybutyl]-3-(hydroxymethyl)-benzonitrile (R/S ratio: 95.7/4.3) by Reaction with different acids in toluene.

General method: R-4-[4-(dimethylamino)-1-(4'-fluorophenyl)-1-hydroxybutyl]-3-(hydroxymethyl)-benzonitrile (67.5 g, R/S ratio: 95.7/4.3) was dissolved in toluene (315 mL). At room temperature, a mixture of acid and ice (or water) was added (the quantities of acid and ice are listed in Table 2). The mixture was stirred at 78–85° C. (the reaction time have been listed in Table 2). The reaction mixture was cooled and water was added. Aqueous ammonia (25% by weight) was added to give a pH 9.5–10.5. The mixture was heated to 50–55° C. (5–10 minutes). The phases were separated and the toluene phase was washed three times with water (3×65 mL). The toluene was removed at reduced pressure at a maximum of 60° C. The product was an oil.

Citalopram was prepared by the general method above. The type of acid and the quantities of acid and water in the mixture are listed in Table 2. The percentage of the citalopram that is S-citalopram, analysed by chiral HPLC, is listed in Table 2 as well.

TABLE 2

Citalopram by reaction with different acids in toluene.

| Example | Acid type | Mass of acid | Mass of ice or water in mixture | Reaction time | Percent S-Citalopram | Yield |
|---|---|---|---|---|---|---|
| 5 | Sulphuric acid | 26 g | 10 g ice | 70 minutes | 73.8 | 61.8 g (97%) |
| 6 | Phosphoric acid | 275 g | 11 g ice | 4 hours | 70.9 | 67.2 g (~100%) |

Example 3

Preparation of Citalopram HBr (racemic) from R-4-[4-(dimethylamino)-1-(4'-fluorophenyl)-1-hydroxybutyl]-3-(hydroxymethyl)-benzonitrile (R/S ratio: 95.7/4.3) by combination of products obtained from the acidic and the basic ring-closure Methods.

Acidic Ring Closure:

R-4-[4-(dimethylamino)-1-(4'-fluorophenyl)-1-hydroxybutyl]-3-(hydroxymethyl)-benzonitrile (67.5 g, R/S ratio: 95.7/4.3) was dissolved in toluene (315 mL). At room temperature, a mixture of sulphuric acid (26 g, 96%) and ice (10 g) was added. The mixture was stirred at 78–85° C. for 2 hours. The reaction mixture was cooled and 40 mL water was added. Aqueous ammonia (25% by weight) was added to give a pH 9.5–10.0. The mixture was heated to 55° C. (10 minutes). The phases were separated and the toluene phase was washed three times with water (3×65 mL). The toluene was removed at reduced pressure at a maximum of 60° C. to give an oil (oil A). Yield: 63 g (99%).

Basic Ring Closure of Labile Ester:

R-4-[4-(dimethylamino)-1-(4'-fluorophenyl)-1-hydroxybutyl]-3-(hydroxymethyl)-benzonitrile (33.7 g, R/S ratio: 95.7/4.3) was dissolved in acetonitrile (16 g) and toluene (135 mL). 21.4 g Triethylamin was added. A solution of tosylchlorid (19.7 g) and toluene (55 mL) was added to the mixture at a rate so that the temperature was kept bellow 50° C. The mixture was stirred at 10° C. for 20 minutes. Water (75 mL) was added and the mixture was stirred for 5 minutes. Aqueous ammonia (25% by weight) was added to give a pH of 9.5. The phases were separated and toluene (35 mL) was added to the water phase. This was stirred for 10 minutes at 45° C. The toluene phases were combined and washed with water (2×75 mL). The toluene was removed at reduced pressure at a maximum of 50° C. to give an oil (oil B). Yield: 32.3 g (~100%).

Precipitation of a Mixture of Oils A and B.

Oil A (57 g) and oil B (28 g) were mixed by dissolving in acetone (310 mL) at room temperature. 35 mL of the solution was removed, HPLC showed an S/R ratio of 49.6/50.4. The mixture was cooled. Gaseous hydrogen bromide was added until pH was 1.5. 15 mL of the removed solution were then re-added to the mixture, adjusting the pH to 3–4.5. The mixture was cooled to 15° C. and stirred overnight. The crystals were filtered and washed with a mixture of acetone (70 mL) and hexane (70 mL). After drying, a yield of 75.7 g (71%) crystals was obtained. The purity of the crystals was 99.2% (HPLC) and the S/R ratio was 49.5/50.5 (Chiral HPLC).

Recrystallisation in Water

Crystals (29.9 g) from the precipitation of oils A and B were dissolved in 75 mL water at about 48° C. The solution was cooled and seeded, and it was stirred for 2½ day at room temperature. The mixture was cooled to 8° C. The crystals were filtered off and washed with water (24 mL). After drying, a yield of 27.9 g (93.3%) Citalopram HBr (racemic) was obtained. The purity of the crystals was 99.4% (HPLC) and the S/R ratio was 50/50% (Chiral HPLC), hence a racemic substance was obtained.

Example 4

Preparation of S-citalopram oxalate from R4-[4-(dimethylamino)-1-(4'-fluorophenyl)-1-hydroxybutyl]-3-(hydroxymethyl)-benzonitrile (R/S ratio: 95.7/4.3).

Ring Closure in Presence of Sulphuric Acid

R-4-[4-(dimethylamino)-1-(4'-fluorophenyl)-1-hydroxybutyl]-3-(hydroxymethyl)-benzonitrile (67.0 g, R/S ratio: 95.7/4.3%) was dissolved in toluene (315 mL). At room temperature, a mixture of sulphuric acid (25 g, 96%) and ice (10 g) was added. The mixture was stirred at 80–85° C. for 1 hour and 40 minutes. The reaction mixture was cooled to room temperature and water (40 mL) was added. Aqueous ammonia (50 mL, 25% w/w) was added to adjust pH to 10.5. The mixture was heated to 55° C. (10 minutes). The phases were separated and the toluene phase was washed three times with water (3×65 mL). The toluene was removed at reduced pressure at a maximum of 60° C. to an oil. Yield: 60.4 g (95%).

The oil (60.4 g) was dissolved in heptane (600 mL) by heating to 89° C. The mixture was allowed to cool to room temperature and stirred over-night. The mixture was filtered. The mother liquor was evaporated and the yield was 20.4 g (34%). The mother liquor was dissolved in ethanol (78 mL) and the mixture was cooled to <25° C. A solution of oxalic acid anhydrate (10.2 g) in ethanol (48 mL) was added. The mixture was stirred for 3 hours at <15° C. The mixture was filtered and washed with ethanol (24 mL). After drying, a yield of 19.9 g (76%) was obtained. The purity of the crystals was 96.8% (HPLC) and the S/R ratio was 97.6/2.4 (Chiral HPLC).

Example 5

Preparation of Citalopram from R-4-[4-(dimethylamino)-1-(4'-fluorophenyl)-1-hydroxybutyl]-3-(hydroxymethyl)-benzonitrile (R/S ratio: 69.0/31.0) by reaction with sulphuric acid in acetonitrile.

R-4-[4-(dimethylamino)-1-(4'-fluorophenyl)-1-hydroxybutyl]-3-(hydroxymethyl)-benzonitrile (31.1 g, R/S ratio: 69.0/31.0) dissolved in acetonitrile (420 g) was stirred at room temperature and a mixture of sulphuric acid (50 g, 96%) and ice (17 g) was added. The mixture was stirred at 78–80° C. for 1 hour. The reaction mixture was cooled and water and toluene (160 mL) were added. Aqueous ammonia (25% by weight) was added to give a pH of 10.5. The mixture was heated to 50–55° C. (5–10 minutes). The phases were separated and to the water phase was added toluene (25 mL) and it was stirred at 50–55° C. (5–10 minutes). The phases were separated and the combined toluene phases were washed three times with water (3×50 mL). The toluene was removed at reduced pressure at a maximum of 60° C. The product was an oil. Yield: 32.9 g (90%). The purity of the evaporated mother liquor was 96.9% and the S/R ratio was 59.5/40.5 (Chiral HPLC).

Example 6

Preparation of Citalopram from S-4-[4-(dimethylamino)-1-(4'-fluorophenyl)-1-hydroxybutyl]-3-(hydroxymethyl)-benzonitrile (S/R ratio: 99.1/0.9) by reaction with sulphuric acid in toluene.

S-4-[4-(dimethylamino)-1-(4'-fluorophenyl)-1-hydroxybutyl]-3-(hydroxymethyl)-benzonitrile (67.0 g, S/R ratio: 99.1/0.9) was dissolved in toluene (315 mL). At room temperature a mixture of sulphuric acid (25.8 g, 96% and ice (10.7 g) was added. The mixture was stirred at 78–85° C. for 2 hours. The reaction mixture was cooled and water (40 mL) was added. Aqueous ammonia (50 mL, 25% by weight) was added to give a pH 10.5–11.0. The mixture was heated to 57° C. (10 minutes). The phases were separated and the toluene phase was washed three times with water (3×65 mL). The toluene was removed at reduced pressure at a maximum of 60° C. The product was an oil. Yield: 63.9 g (~100%). The purity of the oil was 94.9% and the S/R ratio was 26.3/73.7 (Chiral HPLC).

Example 7

Purification of S-Citalopram by Precipitation of the Free Base

Precipitation experiments were conducted to determine how efficient the process was for the removal of small amounts of mixtures R- and S-citalopram from S-citalopram. See Table 3 for the results. The general procedure was as follows. To a mixture of S- and R-citalopram (as described in the "Before precipitation" column) was added heptane (10 mL/1 g citalopram). The mixtures were warmed to reflux, whereupon the citalopram samples dissolved. Heating was stopped, and the samples were allowed to cool to room temperature slowly. In all cases, some material fell out of solution. Where there was a large amount of the R-citalopram in the starting material, the residue was generally a solid, but where there was only a small amount of the R-citalopram in the starting material, the residue was generally an oil. In all cases the mother liquor was removed by filtration (or decanting, in the case of an oily precipitate). The R/S ratios of the precipitates are shown in Table 3. The filtrates were evaporated to give oils/amorphous solids. The R/S ratios of these oils/amorphous solids are shown in the columns "Oil/amorphous solid after evaporation" in Table 3. In all cases, the products were analysed by chiral SCFC HPLC.

TABLE 3

Precipitation of the free racemic citalopram base

| Before Precipitation Mixture of Isomers | | After Precipitation | | | |
|---|---|---|---|---|---|
| | | Precipitate (mixture of R and S-citalopram) | | Oil/amorphous solid after evaporation (enriched S-enantiomer) | |
| S % | R % | S % | R % | S % | R % |
| 98.2 | 1.8 | 99 | 1.3 | 98.1 | 1.9 |
| 97.5 | 2.5 | 98 | 2.5 | 96.9 | 3.1 |
| 95.4 | 4.6 | 82 | 17.6 | 98.8 | 1.2 |
| 94.2 | 5.8 | 66 | 34 | 98.5 | 1.5 |
| 89.0 | 11 | 65 | 35 | 98.5 | 1.5 |
| 80.3 | 19.7 | 54 | 46 | 98.4 | 1.6 |
| 61.0 | 39 | 53 | 47 | 96.7 | 3.3 |

Inspection of the last 5 rows in Table 3 shows that when the ratio S/R in the starting material is less than 97/3, a substantial enrichment of the S-isomer occurs in the oil after evaporation of the filtrate. In all cases, the ratio of S/R in the final product is >95/5.

Example 8

Purification of S-Citalopram by Precipitation of Citalopram as the Hydrobromide Salt A mixture of citalopram isomers was dissolved in isopropyl alcohol (IPA) (10 ml IPA/1 g citalopram). A solution of anhydrous HBr in IPA (2.0 eq, 5.2 M) was added dropwise, and the solutions were seeded with racemic citalopram HBr crystals. The solutions were stirred overnight and filtered. The filtrate was evaporated to give an oil/amorphous solid. The results of these experiments are shown in Table 4. "Before Precipitation" refers to the composition of the mixture before addition of HBr, and "After Precipitation" refers to the two products isolated after filtration. No crystalline material was isolated in the first case (where the "Mixture of Isomers" was S: 98.2% and R: 1.8%). The products were analysed by chiral SCFC HPLC.

TABLE 4

Crystallisation of citalopram HBr salt

| Before Precipitation Mixture of Isomers | | After Precipitation | | | |
|---|---|---|---|---|---|
| | | Crystalline solid from IPA (mixture of R and S-citalopram) | | Oil after evaporation of IPA (enriched S-citalopram) | |
| S % | R % | S % | R % | S % | R % |
| 98.2 | 1.8 | | | 98.7 | 1.3 |
| 97.5 | 2.5 | 75 | 25 | >99.9 | <0.1 |
| 95.4 | 4.6 | 69 | 31 | >99.9 | <0.1 |
| 94.2 | 5.8 | 68 | 32 | >99.9 | <0.1 |
| 89.0 | 11 | 69 | 31 | >99.9 | <0.1 |
| 78.7 | 21.3 | 65 | 35 | 98.9 | 1.1 |
| 80.3 | 19.7 | 60 | 40 | 98.4 | 1.6 |
| 61.0 | 39 | 56 | 44 | 96.7 | 3.3 |

In almost all cases, there was virtually no R-isomer remaining in the mother liquor, and the yield of the precipitates and the oils after evaporation reflect this. Inspection of the first column and the second last column indicates that in most cases, substantial enrichment of the S-isomer occurred, and that in all cases the S/R ratio of the oil after evaporation was greater than 96/4.

The invention claimed is:

1. A process for the preparation of racemic citalopram free base or an acid addition salt thereof and R- or S-citalopram as the free base or an acid addition salt thereof from non-racemic citalopram comprising the steps of:
   i) precipitating citalopram as the free base or as an acid addition salt thereof from a solution of non-racemic citalopram, wherein the precipitated citalopram comprises racemic citalopram and the mother liquor comprises R- or S-citalopram;
   ii) separating the precipitate from the mother liquor;
      iia) if the precipitate is crystalline, optionally recrystallizing the precipitate one or more times to form racemic citalopram, and then optionally converting the precipitate into an acid addition salt thereof;
      iib) if the precipitate is not crystalline, optionally repeating the precipitation of step i) and the separation of step ii) until a crystalline precipitate is obtained, optionally recrystallizing the crystalline precipitate one or more times to form racemic citalopram, and then optionally converting the precipitate into an acid addition salt thereof;
   iii) optionally subjecting the mother liquor to further purification;
   iv) isolating R- or S-citalopram from the mother liquor and optionally converting the R- or S-citalopram into an acid addition salt thereof.

2. A process for the preparation of S-citalopram or R-citalopram from non-racemic citalopram, comprising the steps of:
   i) precipitating citalopram as the free base or as an acid addition salt thereof from a solution of non-racemic citalopram, wherein the precipitated citalopram comprises racemic citalopram and the mother liquor comprises S- or R-citalopram;
   ii) separating the precipitate from the mother liquor;
   iii) optionally subjecting the mother liquor to further purification;
   iv) isolating S- or R-citalopram from the mother liquor and optionally convening the S- or R-citalopram into an acid addition salt thereof.

3. A process according for the preparation of racemic citalopram from non-racemic citalopram, comprising the steps of:
   i) precipitating citalopram as the free base or as an acid addition salt thereof from a solution of non-racemic citalopram, wherein the precipitated citalopram comprises racemic citalopram and the mother liquor comprises S- or R-citalopram; and
   ii) separating the precipitate from the mother liquor;
      iia) if the precipitate is crystalline, optionally recrystallizing the precipitate one or more times to form racemic citalopram, and then optionally converting the precipitate into an acid addition salt thereof;
      iib) if the precipitate is not crystalline, repeating the precipitation of step i) and the separation of step ii) until a crystalline precipitate is obtained, optionally recrystallizing the crystalline precipitate one or more times to form racemic citalopram, and optionally converting the precipitate into an acid addition salt thereof.

4. The process according to claim 1, wherein citalopram is precipitated using an acid.

5. The process according to claim 1, wherein the salt is precipitated in step i) as the hydrobromide salt.

6. The process according to claim 1 wherein, the free base is precipitated in step i).

7. The process according to claim 1, wherein non-racemic citalopram contains more than 50% of S-citalopram.

8. The process according to claim 7, wherein S citalopram is isolated from the mother liquor by evaporation and thereafter optionally converted to an acid addition salt thereof.

9. The process according to claim 7, wherein the mother liquor is acidic and S-citalopram is isolated from the mother liquor by basifying the mother liquor, followed by phase separation or extraction with a solvent and evaporation of the solvent, and thereafter optionally converting S-citalopram into an acid addition salt thereof.

10. The process according to claim 1, wherein step iii) comprises subjecting the mother liquor to one or more precipitations of citalopram as described in step i).

11. The process according to claim 1, wherein non-racemic citalopram comprising more than 50% of S-citalopram is prepared from a mixture of R- and S-4-[4-(dimethylamino)-1-(4'-fluorophenyl)-1-hydroxybutyl]-3-hydroxymethyl)-benzonitrile comprising more than 50% of the S-enantiomer by forming a labile ester group and thereafter conducting ring closure in a basic environment.

12. The process according to claim 1, wherein non-racemic citalopram comprising more than 50% of R-citalopram is prepared from a mixture of R- and S-4-[4-(dimethylamino)-1-(4'-fluorophenyl)-1-hydroxybutyl]-3-hydroxymethyl)-benzonitrile comprising more than 50% of the R-enantiomer by forming a labile ester group and thereafter conducting ring closure in a basic environment.

13. The process according to claim 1, wherein non-racemic citalopram comprising more than 50% of S-citalopram is prepared from a mixture of R- and S-4-[4-(dimethylamino)-1-(4'-fluorophenyl)-1-hydroxybutyl]-3-hydroxymethyl)-benzonitrile comprising with than 50% of the R-enantiomer by ring closure in the presence of an acid.

14. The process according to claim 1, wherein non-racemic citalopram comprising more than 50% of R-citalopram is prepared from a mixture of R- and S-4-[4-(dimethylamino)-1-(4'-fluorophenyl)-1-hydroxybutyl]-3-hydroxymethyl)-benzonitrile comprising more than 50% of the S-enantiomer by ring closure in the presence of an acid.

15. A process for the preparation of a mixture of R- and S-citalopram comprising more than 50% of the S-enantiomer, comprising the step of subjecting a mixture of R- and S-4-[4-(dimethylamino)-1-(4'-fluorophenyl)-1-hydroxybutyl]-3-hydroxymethyl)-benzonitrile comprising more than 50% of the R-enantiomer to ring closure in the presence of an acid.

16. A process for the preparation of a mixture of R- and S-citalopram comprising more than 50% of the R-enantiomer, comprising the step of subjecting a mixture of R- and S-4-[4-(dimethylamino)-1-(4'-fluorophenyl)-1-hydroxybutyl]-3-(hydroxymethyl)-benzonitrile comprising with than 50% of the S-enantiomer to ring closure in the presence of an acid.

17. The process according to claim 12, wherein the starting material contains more than 90% of R-4-[4 (dimethylammo)-1-(4'-fluorophenyl)-1-hydroxybutyl]-3-(hydroxymethyl)-benzonitrile compared to S-4-[4 (dimethylamino)-1-(4'-fluorophenyl)-1-hydroxybutyl]-3-(hydroxymethyl)-benzonitrile.

18. The process according to claim 13, wherein the acid is a mineral acid, a carboxylic acid, a sulfonic acid or a sulfonic acid derivative.

19. The process according to claim 18, wherein the acid is $H_2SO_4$ or $H_3PO_4$.

20. The process according to claim 5, wherein the hydrobromide salt is in crystalline form.

21. The process according to claim 7, wherein the non-racemic citalopram contains more than 90% of S-citalopram.

22. The process according to claim 8, wherein the acid addition salt is the oxalate salt.

23. The process according to claim 9, wherein the acid addition salt is the oxalate salt.

24. The process of claim 13, wherein the starting material contains more than 90% of R-4-[4 (dimethylamino)-1-(4'-fluorophenyl)-1-hydroxybutyl]-3-(hydroxymethyl)-benzonitrile compared to S-4-[4 (dimethylamino)-1-(4'-fluorophenyl)-1-hydroxybutyl]-3-(hydroxymethyl)-benzonitrile.

25. The process of claim 15, wherein the starting material contains more than 90% of R-4-[4 (dimethylamino)-1-(4'-fluorophenyl)-1-hydroxybutyl ]-3-(hydroxymethyl)-benzonitrile compared to S-4-[4 (dimethylamino)-1-(4'-fluorophenyl)-1-hydroxybutyl]-3-(hydroxymethyl)-benzonitrile.

26. The process according to claim 1, wherein the mother liquor is subjected to further purification.

27. The process according to claim 2, wherein the mother liquor is subjected to further purification.

* * * * *